(12) United States Patent
Kogan

(10) Patent No.: US 12,714,761 B1
(45) Date of Patent: Aug. 25, 2026

(54) UNIVERSAL UV DISINFECTION DEVICE

(71) Applicant: Iakov Kogan, Etobicoke (CA)

(72) Inventor: Iakov Kogan, Etobicoke (CA)

(73) Assignee: Invisible Power Inc., Thorold (CA)

( * ) Notice: Subject to any disclaimer, the term of this patent is extended or adjusted under 35 U.S.C. 154(b) by 1009 days.

(21) Appl. No.: 17/395,932

(22) Filed: Aug. 6, 2021

(51) Int. Cl.
*A61L 2/10* (2006.01)
*A61L 2/24* (2006.01)
*A61L 2/26* (2006.01)

(52) U.S. Cl.
CPC .................................... *A61L 2/10* (2013.01); *A61L 2/24* (2013.01); *A61L 2/26* (2013.01); *A61L 2202/11* (2013.01); *A61L 2202/14* (2013.01); *A61L 2202/16* (2013.01); *A61L 2202/25* (2013.01)

(58) Field of Classification Search
CPC ..... A61L 2/10; A61L 2/24; A61L 2/26; A61L 2202/11; A61L 2202/14; A61L 2202/16; A61L 2202/25
See application file for complete search history.

(56) References Cited

U.S. PATENT DOCUMENTS 7,507,980 B2 3/2009 Garcia et al.
8,617,464 B2 12/2013 Kerr
2012/0168647 A1* 7/2012 Davis ........................ A61L 2/10 250/492.1
2017/0351142 A1* 12/2017 Imaoku ................ G02B 6/0036
2021/0353799 A1* 11/2021 Spears ...................... A61L 2/26

FOREIGN PATENT DOCUMENTS

WO WO 2009/065128 5/2009

OTHER PUBLICATIONS

Tianghong Dai et al., "Ultraviolet C irradiation: an alternative antimicrobial approach to localized infections?", Expert Rev Anti Infect Ther. 2012 10(2): 185-195 (Year: 2012).*

* cited by examiner

*Primary Examiner* — Jennifer Wecker
*Assistant Examiner* — Brady C Pilsbury

(57) ABSTRACT

This invention proposes a multifunctional UV disinfection device that can be used as a handheld to sanitize personal items, as a UV broom to disinfect floors, and as a mobile to disinfect hotel rooms, medical offices, transportation vehicles, washrooms, schools, stores, and sport facilities. The device has an elongated shape, consists of two units, and compact to be convenient for business and leisure travel. One or more UV radiation units can be mounted through an elongated handle to an extendable pole, a flat surface, a moving stand, a piece of furniture, a cleaning machine and a robot.

16 Claims, 8 Drawing Sheets

UNIVERSAL UV DISINFECTION DEVICE

FIELD OF THE INVENTION

This invention relates to the area of UV disinfection devices for sanitizing personal items, large flat areas and air.

BACKGROUND OF THE INVENTION

The Covid-19 pandemic has created unprecedented demand for disinfection technologies. The virus is mutating at the faster rate than vaccination, and the virus is unlikely to go away soon. The UV disinfection techniques are an effective solution in fighting pandemic. Unlike vaccines the UV radiation is not specific, and effective against broad range of infectants.

In the absence of pandemic many homes and businesses might suffer from infestations such as molds, viruses and bacteria. Carpets at homes and hotels can contain bio and organic substances potentially unhealthy for humans. The outer surfaces of suitcases, hand bags, briefcases, can come in contact with contaminated areas in airport bathrooms, bars and restaurants. The soles and heels of footwear are exposed to microbial contamination at stores, offices, hospitals and public toilets. These subjects can further spread bacteria in the uncontaminated areas.

Conventional cleaning does not effectively eliminate infestation agents. Chemical disinfectants are toxic and environmentally unfriendly. Steam cleaning of carpets is expensive, and can also involve the use of intoxicants. UV radiation is a unique technology for effective cleaning large polluted areas.

Ultraviolet radiation is classified into three wavelength ranges: UVA, from 315 nm to 400 nm; UVB, from 280 nm to 315 nm, and UVC, from 100 nm to 280 nm. UVC radiation is the most effective for deactivation of bacteria and other pathogens. The mechanism of UVC inactivation of microorganisms is based on the damage of the genetic material in the nucleus of the cell or nucleic acids in the virus Tianhong Dai et al, 2012. The UVC spectrum, especially in the range of 250-270 nm, is strongly absorbed by the nucleic acids of a microorganism and, therefore, is the most lethal range of wavelengths known as the germicidal spectrum. The light-induced damage to the DNA and RNA of a microorganism results from the dimerization of pyrimidine molecules. In particular, thymine (which is only found in DNA) produces cyclobutane dimers. When thymine molecules are dimerized, it becomes very difficult for the nucleic acids to replicate, and if replication does occur, it often produces a defect that prevents the microorganism from being viable. The dosage of the UV radiation is a function of the time of exposure of radiation to the cleaning medium. The radiation intensity should be multiplied by time to get the dose. Usually 10 $mJ/cm^2$-50 $mJ/cm^2$ UVC light required for disinfection.

There are two major optical elements that emit in UVC range: an electroluminescent lamp (EL) and a UV light emitting diode (LED). The EL is less expensive, and better suitable for high power devices. Mechanism of emission is based on gas discharge in vacuumed silica cylinder filled with mercury drops. The system also contains ballast, which main function is to prevent uncontrolled increase in current. An EL can emit at 253.7 nm and 185 nm. 185 nm radiation produces ozone, one of the strongest oxidants. While UV light damages viruses and bacteria in direct visibility, ozone penetrates hidden areas, pores of fabric and increases the effectiveness of disinfection.

Recently much interest has been drawn by krypton-chlorine (used instead mercury) EL lamps with emission at 222 nm. The shorter UV wavelength, the smaller is radiation penetration into the human skin. The EL lamps with 222 nm emission are much safer for humans while still high effective against bacteria and viruses.

A UVC LED based on modern semiconductor gallium indium nitride is the most advanced solution for UV disinfection. Typical LED is a small size (for example 3.5 mm*3.5 mm*1.5 mm) surface mount element that emits UV light in the range 265 nm-280 nm. The element needs 6V-7V power supply.

Ken V. Garcia US. et al, U.S. Pat. No. 7,507,980 have proposed a UV disinfection device for sanitizing carpets. The device is a combination of a vacuum cleaner and a UV disinfection device, has complex design, is not compact, and cannot be used for disinfection of personal items and air.

James Kerr, U.S. Pat. No. 8,617,464, patented a UV sanitizing devices for footwear, bags, purses etc. The device includes a flexible bag with UVC absorbing liquid. When a subject is placed on the upper panel it makes the layers of liquid absorber thin, and UV light can reach the subject. The problem is that in case of relatively large not flat objects the radiation intensity in some areas might not be sufficient for disinfection. The device is split in to two sections, but the sections are not detachable. The bag with absorbinger liquid is replaceable to eliminate leakage. The device is not universal, and unsuitable for disinfection of large areas of floors.

Darrick Kim and John Paoll, WO Pat. Appl. 2009/065128 proposed a UV disinfection devices for sanitizing shoes (FIG. 2 of WO Pat. Appl. 2009/065128). The applicants also suggested a hand push device with wheels for sanitizing mats in sport facilities (FIG. 5 of WO Pat. Appl. 2009/065128), and a surface mountable UV radiation device for sanitizing countertops in kitchens, bathrooms, health facilities and nurseries (FIG. 12A-12E of WO Pat. Appl. 2009/065128). It is important that the applicants proposed completely different designs united under one claim 1, which covers any UV disinfection device. In reality no universal disinfection device was demonstrated. The device indicated in FIG. 5 of WO Pat. Appl. 2009/065128 includes wheels, and can be used for disinfection of floors, but cannot be applied for disinfection of walls, and personal items. The device indicated in FIG. 2 (WO Pat. Appl. 2009/065128) can be used for shoe disinfection, but cannot be applied to sanitize floors or air. Wall mounted devices in FIG. 12A-12E (WO Pat. Appl. 2009/065128) can be used for sanitizing air, but cannot be applied for floor disinfection. The devices cannot be combined in one universal and compact unit.

The main disadvantage of known UV disinfection devices is the lack of universality. While many devices are portable they are not compact and are expensive in production. No appropriate design has been described therefore leaving those skilled in the art to perform a substantial amount of research to find a new solution.

The requirements for design of an advanced UV disinfection device are as follows:

a) the device should have a simple design, and to be manufactured at low cost
b) the device should be universal to fulfill several major operations
c) the device is expected to be compact, and suitable for travel and transportation
d) the device should be produced from lightweight low cost UV stable materials e) the users should be protected from direct radiation if no remote control is used f) the device for air disinfection is expected to have the largest possible angle of emission, and to be controlled remotely g) the UV emitting element is aging during operation, and the design should be suitable for simple replacement of the UV emitting element

BRIEF SUMMARY OF THE INVENTION

This invention proposes a multifunctional portable UV disinfection device that can be used as a handheld (FIG. 4) to sanitize personal items, as a UV broom to disinfect mats, floors and walls, and as a mobile/stationary installation to disinfect air. The device is compact and portable to be convenient for business and leisure travel.

The device has an elongated shape and includes two units 1, 2 (FIG. 1, 2) joined to each other, and the unit 2 is detachable from the unit 1 by the user. The unit 1 includes the UV radiation assembly comprising the UV emitting element 3, the bracket 4 accommodating the power supply, the platform 5 and the elongated handle 6. The unit 2 includes the cover 7, and two caster wheels 8.

An expandable pole 10 (FIG. 5) can be attached to the handle to use the device for sanitizing the floors and the walls, FIG. 6. Air disinfection requires large angle of radiation. For this purpose the unit 2 is separated from the unit 1. The unit 1 has wide angle of UV radiation, and can be fixed to a stand 11, FIG. 7 using the elongated handle 6.

The UV device can be used as a part of a cleaning machine, a stationary/mobile stand, and a robot. The device can be fixed to a piece of furniture.

In the absence of the access to electricity, the device modification shown in FIG. 8 can be powered with the battery 13 equipped with the inverter 14, and mounted on the second platform 12 fixed to the handle 6. The 8 W device, the expandable pole and the stand can be stored in the box with the size 4 in*4 in*18 in. The disinfection device with the 40 W EL UV emitting element can be packed in the box 4 in*4 in*24 in.

DETAILED DESCRIPTION OF THE INVENTION

Figure 1:
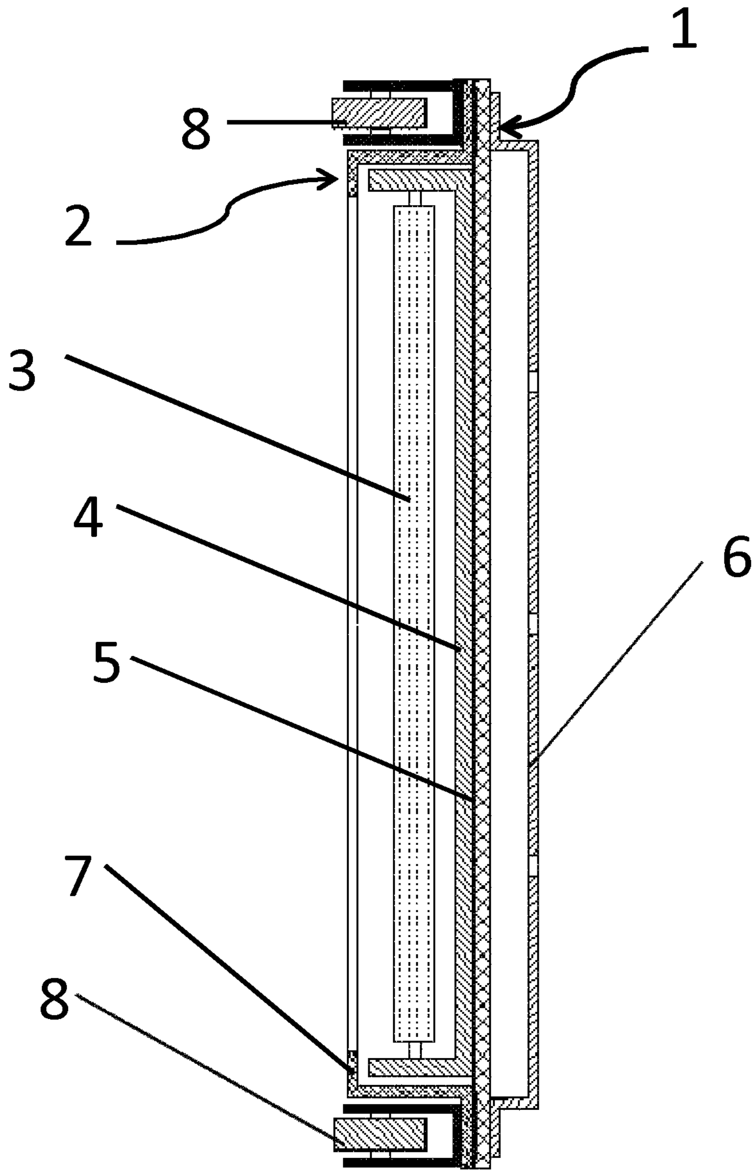
FIG. 1 shows the schematic of the UV disinfection device. The device comprises units 1 and 2. The first unit 1 includes the UV emitting element 3, the bracket 4, platform 5, and the handle 6. UV emitting element 3 and bracket 4 with the embedded power supply (not shown) form the UV radiation assembly. The unit 2 includes cover 7 and the caster wheels 8.
Figure 2:
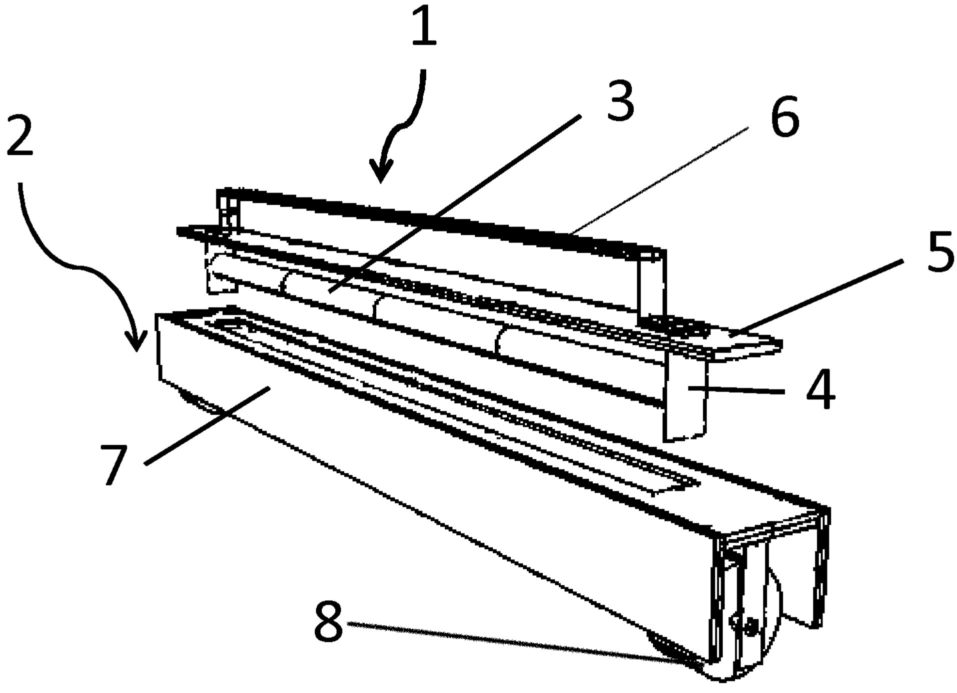
FIG. 2 shows the photo of the UV disinfection device of this invention when the unit 2 is detached from the unit 1.
Figure 3:
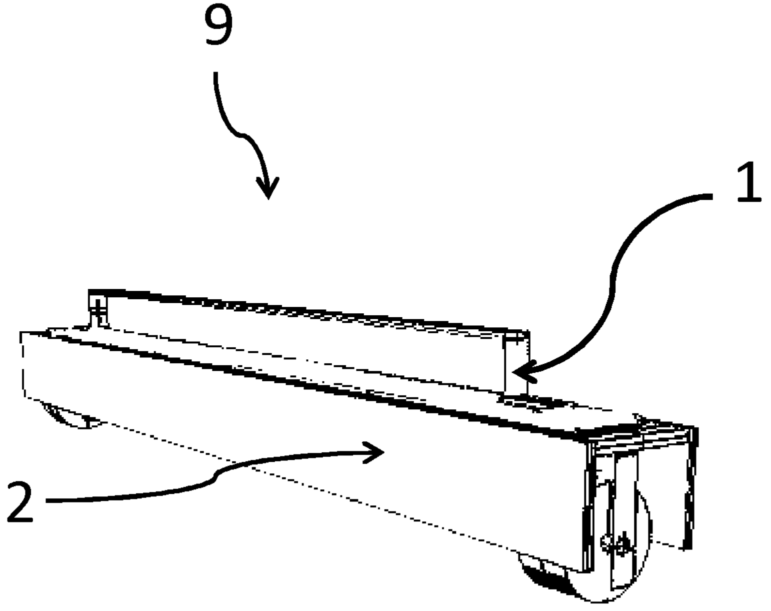
FIG. 3 shows the photo of the assembled UV disinfection device when the unit 2 is fixed to the unit 1.
Figure 4:
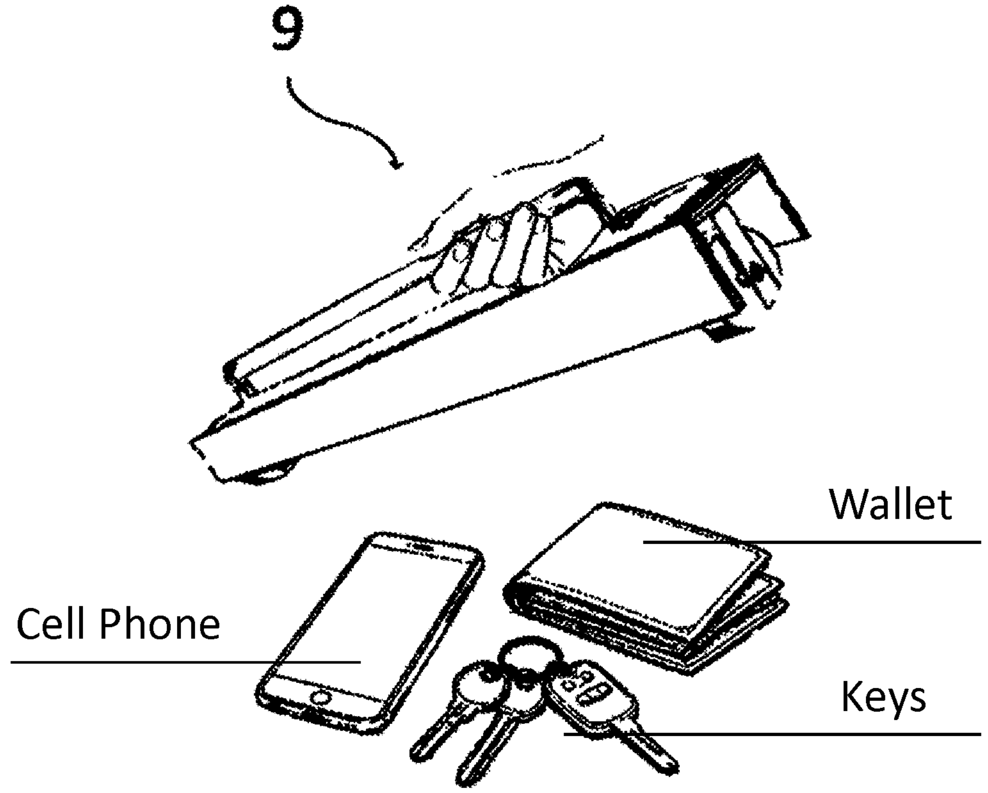
FIG. 4 demonstrates the use of the UV disinfection device 9 as the handheld sanitizer.
Figure 5:
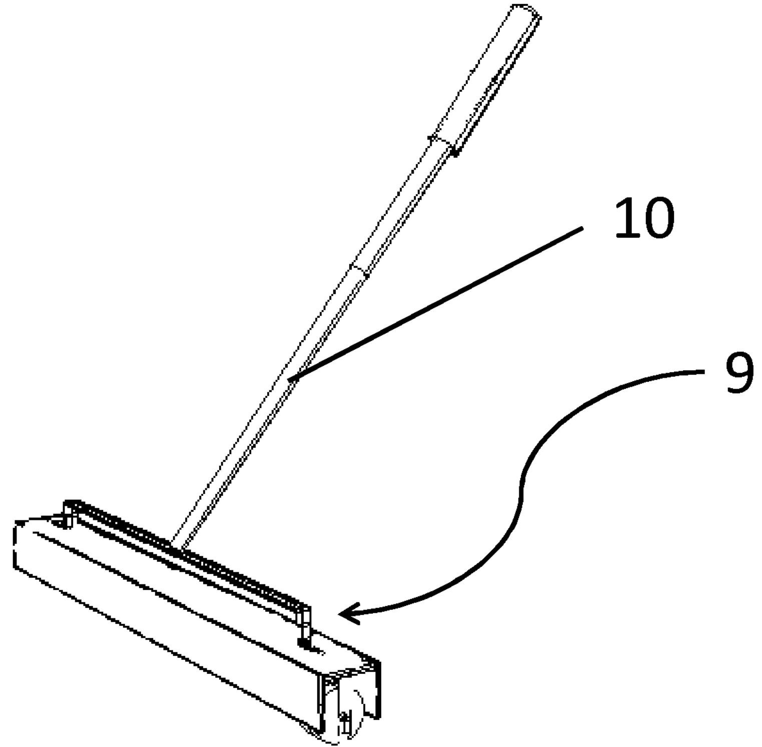
FIG. 5 shows the UV broom based on the UV disinfection device 9 with the extendable and detachable pole 10.
Figure 6:
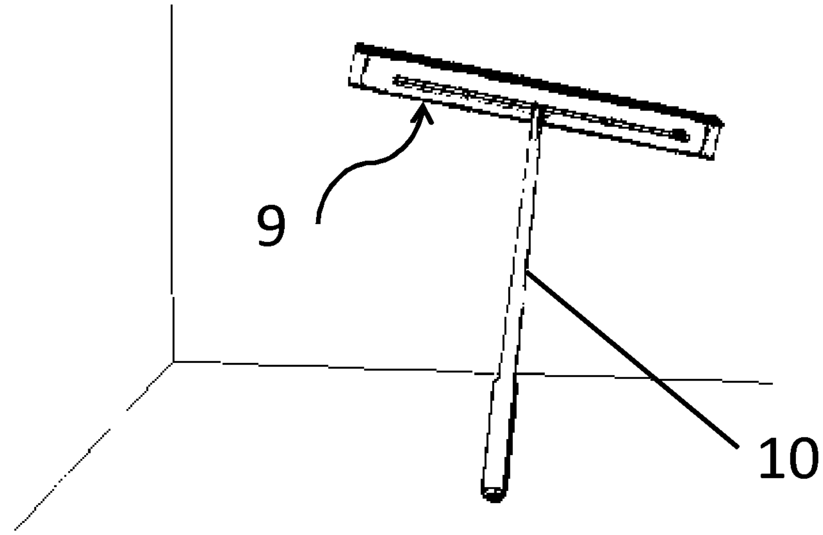
FIG. 6 demonstrates the use of the UV broom for sanitizing walls.
Figure 7:
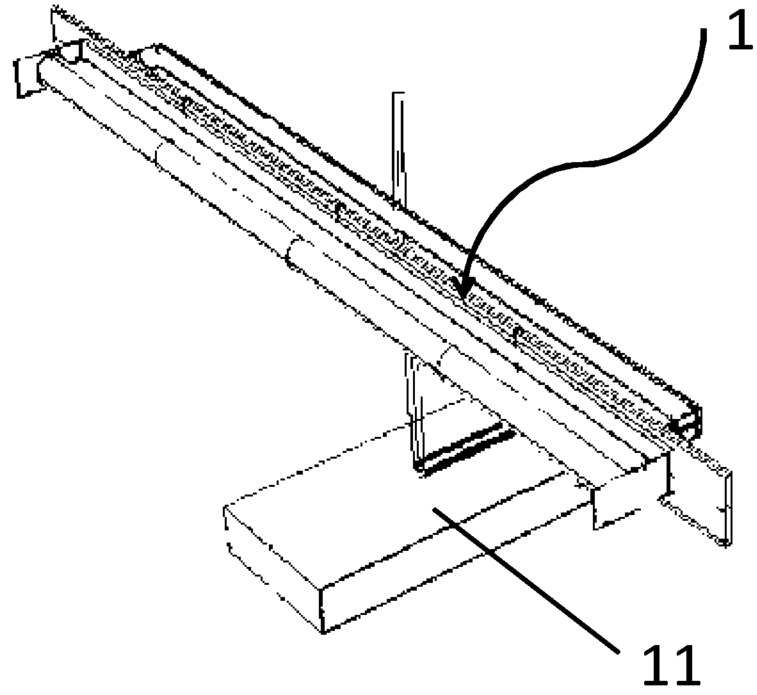
FIG. 7 shows the unit 1 of the UV disinfection device 9 fixed to the stand 11 for sanitizing air.

The multifunctional UV disinfection device has an elongated shape and includes 2 units ((FIG. 1, 2). The base unit 1 includes the UV radiation assembly comprising the UV emitting element 3, the bracket 4 accommodating the power supply, the platform 5 and the elongated handle 6. The unit 2 detachable by the user comprises the cover 7 and two caster wheels 8. Two caster wheels 8 fulfill two functions: on one hand they assure moving the device along the surface (floor, wall, windows etc.), on the other they define the distance between the UV emitting element 3 and the surface. These wheels prevent the damage of the UV emitting element when the element is made of glass. The sizes of the wheels are in the range of 1 in-2 in. The caster wheels are fixed to the upper surface of the cover 7, and U shape metal brackets positioned between the caster wheels and the platform (not shown in the figure) can be used to change the position of the wheels 8. Simple removal of the unit 2 is convenient for the replacement or maintenance of the UV bracket and the UV emitting element.

There is a big difference between the handheld device, the UV broom and the air disinfection installation. It requires about 30 min-60 min to carry out air disinfection in a confined space while the handheld device and the UV broom perform disinfection of the flat surface in a fraction of a second.

An extendable pole can be fixed to the central hole of the elongated handle to use the UV disinfection device as a broom. The expandable pole designed for photography is usable as the extendable pole for the UV disinfection device. The pole is fixed to the handle with a nut, and can be mounted in a short period of time.

Two major types of the UV emitting elements can be used: gas discharge EL lamps, and UV LEDs. The gas discharge lamps can be low pressure, medium pressure and high pressure. The EL lamps are low cost, high conversion efficiency up to 40%, and provide low heat generation. The EL lamp is expected to emit in the range 100 nm-300 nm, and the power of UV radiation is in the range 4 W-120 W. The EL lamp requires 120V power supply; it is made of quartz glass transparent to UV radiation.

The power supply embedded into the bracket includes an electronic circuit that operates in the frequency range 60 Hz-100 KHz, and also includes a ballast that limits the lamp current during operation. The increase of frequency elongates the lifetime of the lamp. Conventional EL lamp contains a drop of mercury. The mercury electroluminescent lamp emits at 253.7 nm and 185 nm. 185 nm radiation produces ozone, one of the strongest oxidants. Ozone can be an extra disinfectant, which penetrates hidden areas shielded from the UV radiation. In certain situations, particularly in the case of poor ventilation, the production of ozone should be eliminated. This can be done by deposition of a thin layer of FEP (fluorinated ethylene propylene) or PTFE (polytetrafluoroethylene). FEP and PTFE layers can be deposited from aqueous dispersions of these materials. As an example the deposition of the 0.1 mm-0.3 mm layer of FEP eliminates 185 nm emission almost completely.

An excimer 222 nm krypton-chlorine EL lamp is a possible alternative to the mercury lamp. The advantage of krypton-chlorine lamp is the absence of 185 nm emission that produces ozone. Also 222 nm radiation is much less dangerous to humans.

The platform, the cover and the handle are made of materials stable to UV light. Metals, aluminum and its alloys, anodized aluminum, zinc and its alloys, copper, bronze, silicon bronze, cupronickel, brass, steel, and stainless steel can be used. Some of plastics like PTFE, FEP, polyacrylates are expected to be stable to UV light. Other plastics: polyethylene, polypropylene, polycarbonate, ABS, PVC, epoxy resin can be used as well, but these plastics should be covered with a layer of stable to UV material to eliminate degradation.

Plastics with poor UV stability can be covered with a thin layer (thickness in the range 1 μm-100 μm) of metal. Nickel, cobalt, copper, tin, lead, iron, bismuth, silver, zinc and their alloys will prevent plastic degradation. The metal layers can be deposited by electroless plating. A layer of FEP and PTFE, silicon rubber based composites with carbon, graphite, metal powders; ceramics, glass can be used as the protection layer. For example titanium oxide based composites with mentioned above adhesives can be used as an alternative protection layer. Metal powders are selected from the group consisting of copper, nickel, lead, tin, bismuth, iron, silver, zinc, cobalt, and their alloys.

The reflector increases the light intensity of the UV element by about 30% at the distance about 2 cm-3 cm in front of the emitting element. This invention proposes stainless steel foil as the reflector film instead of aluminum. As an example 304 or 316 stainless steel can be used. The advantage is long term stability of the surface. Aluminum forms a thin oxide film under influence of UV radiation, oxygen and humidity of air. Unlike aluminum stainless steel is stable to oxidation, keeps shiny surface for a long time, and the intensity of reflected radiation is unchanged during the use. The stainless steel foil of 0.05 mm-0.2 mm thickness is fixed on the surface of the bracket under the light emitting element by epoxy glue or by double sided adhesive tape.

The shock absorber should prevent the light emitting element from damage during the operation and transportation. To create a shock absorber the bracket 4 is fixed to the platform 5 using double-sided foam tape with thickness 1 mm-6 mm. This doubled-sided foam fulfills two functions: it is used to join the bracket 4 with the platform 5, and to form a shock absorber at the same time.

The cover protects the lamp from mechanical damage, and prevents the user from direct exposition to UV radiation. The cover holds the caster wheels that help to transfer the handheld UV device into the UV broom. The cover has the shape of an elongated tube, and preferably the shape of a square tube. It includes upper and lower openings; the upper opening accommodates the UV radiation assembly when the unit 2 is fixed to the unit 1, and the lower opening narrows UV radiation flow. Both openings can be formed using a milling machine. Material of the cover can be transparent to visible spectrum, and absorb UV light at the wavelength below 300 nm to protect users from UV emission at 254 nm. Possible transparent tube materials include polymethylmethacrylate and polycarbonate.

The UV disinfection device can be used for air disinfection in a confined space. The angle of UV emission should be as large as possible. For this purpose the unit 2 is detached from the unit 1. It is expected that in the case of air disinfection the user turns on the device remotely to avoid direct exposure to UV radiation. The remote control transmitters are expected to have an indicator signaling that the UV disinfection device is on. It also includes a timer for automated exposure control. It is desirable to have a warning panel when the UV device is on. Such a warning panel can be controlled by the second remote control which is operated by the electronic circuit of the UV disinfection device when the device is working.

The elongated handle has multiple holes that are convenient for fixing the UV disinfection device to a flat surface of a wall, a piece of furniture, a rod, a stand, and a second platform. It helps to mount the UV disinfection device to the bottom of the cleaning machine to enable disinfection concurrently with cleaning. Also it can be fixed to a programmable moving robot to disinfect large areas of airports, schools, stores, sport and entertainment facilities.

The UV emitting element can be fixed horizontally, vertically and at any angle to a moving stand which includes a base and a pole fixed with one end to the base. The pole can be attached vertically or at any angle to the base, and can have branches to increase the effectiveness of disinfection.

Figure 8:
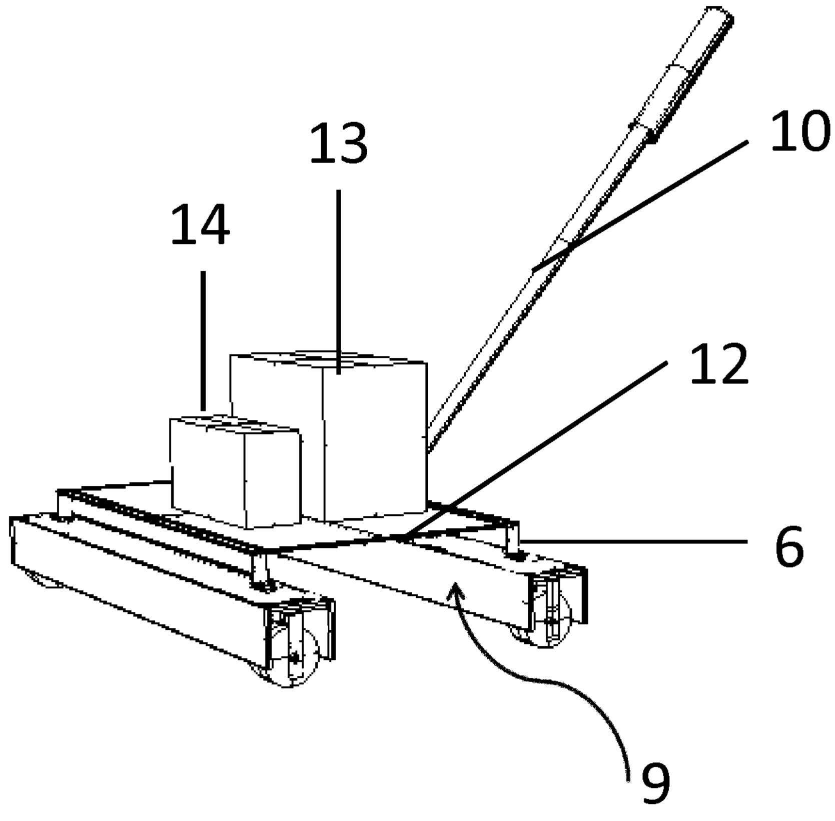
FIG. 8 shows the UV disinfection device 9 with electricity supply from the battery. The battery 13 and the power inverter 14 (12V DC to 120V AC) are mounted on the second platform 12, which is fixed to the handle 6. The second platform 12 includes two additional wheels.

To disinfect large floor areas, and large areas in the absence of access to electricity, the UV disinfection device 9 (FIG. 8) can be powered from a battery. The battery 13 and a power inverter 14 (12V DC to 120V AC) are mounted on the second platform 12, which is fixed to the handle 6. The second platform 12 includes two additional wheels.

It is well known that UVC pulse light has higher disinfection efficiency comparing to continuous radiation. An EL lamp power from 50 Hz-100 KHz electronic power supply can be turned on/off with every power cycle. Emission testing with UVC sensible photodiode demonstrates radiation pulses intact with frequency of the power supply.

A surface mounted UVC LED is a practical alternative to the EL lamp. The UVC LED requires only 6V-7V DC voltage supply. The LED emitting devices can be connected to wires in parallel and, as an alternative, in series. In both cases DC-DC adapters are used to adjust the voltage. Zener diodes can be added in parallel to the LEDs circuit to avoid overvoltage.

Typical LED is a miniature (for example 3.5 mm*3.5 mm*1.5 mm) flat device that emits UV light with wavelength range practically coinciding with the germicidal spectrum. The device needs only 6V-7V power supply. A technology has been developed to produce a UV lighting element based on wires and LEDs soldered to these wires. A ceramic base with groves and rectangular cavities is milled or casted from a liquid ceramic composition. Wires and planar LED's are arranged in the groves and in the rectangular cavities. The wires are prevented from moving by using a cross-bar. Then LEDs are soldered to the wires by hand or automatically. After soldering the wire frame with LEDs is separated from the temporal base. Then the lighting element is soldered to the contacts of the brackets. The power supply is accommodated inside the bracket. Then the UV radiation assembly (LED emitting element connected to the bracket) is used in the same way as the EL radiation assembly.

The UV device of this invention formed of emitting elements radiated in the UVA, UVB, VIS and IR regions can be used for portable lighting, IR heating elements, LCD backlights, photo curing and photo lithography.

The plurality of the first units of Claim 1 can be fixed to a movable stand comprising a base with a plurality of wheels, and a pole with one end fixed to the base. The UV emitting units can be fixed to the pole using holes in the handle at the angle 0°-90°. The base is preferably formed of two elongated plates fixed to each other at the angle 300-90°. The base can also be formed of one plate. The pole can be extended in arbitrary direction using branches.

The UV emitting units preferably include an UVC EL lamp with emission in the range 100 nm-300 nm and radiation intensity 4 W-300 W. The pole is preferably foldable to make disinfection device compact, and convenient for transportation. The device with a 40 W EL emitting element can be packed in the box 4 in*4 in*24 in. The UV disinfection device can be powered from the battery and the inverter fixed to the base. It is possible to use caster wheels and wheels with motors controlled with a microprocessor. The microprocessor program makes it possible automated movement of the stand with the UV emitting units at predetermined speed in predetermined direction. The moving device can provide more effective disinfection because it decreases distance to a subject while the radiation intensity falls proportionally to the square of distance.

The devices of this invention can be broadly used to disinfect rooms in the hotels, transportation vehicles, washrooms, medical offices, schools, stores, and sport facilities.

The invention claimed is:

1. A UV disinfection device comprising a) a UV radiation assembly formed of a UV emitting element, and a bracket accommodating a power supply with electrical contacts to the UV emitting element, and b) a platform holding the UV radiation assembly, and c) a reflector behind the emitting element, and d) a cover, and e) a handle, and f) a shock absorber, and g) a plurality of caster wheels, and h) an optional pole, and i) an optional remote control wherein j) the UV disinfection device comprises two joined units: a first unit includes the UV radiation assembly, the platform, and the handle, and a second unit includes the cover and the plurality of caster wheels, and k) the second unit is detachable from the first unit by the user, and l) the UV disinfection device is multifunctional, and can be used as a handheld to disinfect personal items, as a UV broom to disinfect flat areas, and as a stationary/mobile to disinfect transportation vehicles, medical offices, washrooms, schools, stores, and entertainment facilities, and m) the reflector is made of stainless steel foil, and n) the shock absorber is formed of a double sided foam adhesive tape located between the bracket and the platform, and o) the cover has the shape of a tube with upper and lower openings, the upper opening accommodates the UV radiation assembly when the second unit is fixed to the first unit, and the lower opening narrows UV radiation, and p) the cover includes the plurality of caster wheels fixed to the upper side of the cover, and q) the handle has the shape of an elongated strip with bended ends and multiple holes, and is fixed to the platform, and the holes can be used to fix the UV disinfection device and the first unit to the subjects selected from a group consisting of an extendable pole, a tube, a flat surface, a second platform, a stationary/mobile stand, a piece of furniture, a cleaning machine, and a robot, and r) the UV disinfection device with one emitting element can be packed in a box having a size equal or smaller than 4 in×4 in×24 in with the length of the box proportional to the length of the light emitting element, and s) the remote control is a two way remote control; a first transmitter turns the UV emitting element on, a second transmitter makes a warning sign flashing when the emitting element is on.

2. The UV disinfection device of claim 1 wherein the platform, the cover and the handle are made of materials selected from the group consisting PTFE, FEP, polyacrylates, polyethylene, polypropylene, polycarbonate, ABS, PVC, epoxy resin, carbon composite materials, aluminum and its alloys, anodized aluminum, zinc and its alloys, copper, bronze, silicon bronze, cupronickel, brass, steel, stainless steel, rubber and rubber composites, ceramics, and glass.

3. The UV disinfection device of claim 1 wherein the cover has the shape of a square tube.

4. The UV disinfection device of claim 1 wherein the cover is transparent to visible light, but absorbs radiation with wavelengths bellow 300 nm.

5. The UV disinfection device of claim 1 wherein the UV emitting element is an electroluminescent lamp (EL) with an emission having a wavelength in the range of 100 nm-400 nm, and a power in the range 4 W-300 W.

6. The UV disinfection device of claim 5 wherein electricity to the power supply of the electroluminescent lamp is provided by a battery with an inverter and the battery is positioned on the second platform fixed to the elongated handle.

7. The UV disinfection device of claim 1 wherein the UV disinfection device is compact, and can be packed in a box having a size equal to or smaller than 4 in×4 in×18 in.

8. The UV disinfection device of claim 1 wherein the device has at least 2 and at most 4 caster wheels.

9. The UV disinfection device of claim 1 wherein the UV emitting element is covered with a 0.1 mm-0.3 mm layer of FEP that eliminates UV radiation below 200 nm.

10. The UV disinfection device of claim 1 wherein the thickness of the shock absorber is in the interval 0.25 mm-6 mm.

11. The UV disinfection device of claim 1 wherein the UV radiation is emitted in pulses, wherein the pulses have a frequency of 50 Hz-10 kHz.

12. The UV disinfection device of claim 1 wherein the UV emitting device is made of a plurality of light emitting diodes with an emission having a wavelength in the range of 260 nm-285 nm.

13. The UV disinfection device of claim 1 wherein the platform, the cover and the handle are covered with a layer of a UV stable composition comprising a) an adhesive selected from a group consisting of FEP, PTFE, polyacrylic, polysilicone and b) a UV absorbing material selected from the group consisting of metals, semiconductors, ceramics, graphite, carbon, glass, plastics, and mixtures thereof.

14. The UV disinfection device of claim 1 wherein the platform, the cover and the handle are covered with a thin layer of a UV stable metal selected from the group consisting of copper, nickel, lead, tin, bismuth, iron, silver, zinc, cobalt, and their alloys deposited by electroless plating.

15. The plurality of the UV disinfection devices of claim 1 wherein the devices are fixed to a pole of a stationary/movable stand at an angle 0°-90° using the holes in the elongated handles.

16. The plurality of the UV disinfection devices of claim 15 wherein the UV emitting assemblies are powered from a battery and an inverter fixed to the platform.

* * * * *